United States Patent
Kaneko et al.

(10) Patent No.: US 10,451,701 B2
(45) Date of Patent: Oct. 22, 2019

(54) MAGNETIC RESONANCE IMAGING DEVICE, AND DETERMINATION METHOD FOR HIGH-FREQUENCY MAGNETIC FIELD CONDITIONS

(71) Applicant: Hitachi, Ltd., Tokyo (JP)

(72) Inventors: Yukio Kaneko, Tokyo (JP); Hideta Habara, Tokyo (JP); Yoshihisa Soutome, Tokyo (JP); Yoshitaka Bito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 940 days.

(21) Appl. No.: 14/417,801

(22) PCT Filed: Jul. 24, 2013

(86) PCT No.: PCT/JP2013/070087
§ 371 (c)(1),
(2) Date: Jan. 28, 2015

(87) PCT Pub. No.: WO2014/021172
PCT Pub. Date: Feb. 6, 2014

(65) Prior Publication Data
US 2015/0241539 A1  Aug. 27, 2015

(30) Foreign Application Priority Data
Aug. 3, 2012 (JP) .................... 2012-173348

(51) Int. Cl.
*G01V 3/00* (2006.01)
*G01R 33/565* (2006.01)
(Continued)

(52) U.S. Cl.
CPC .......... *G01R 33/5659* (2013.01); *A61B 5/055* (2013.01); *G01R 33/34092* (2013.01); *G01R 33/385* (2013.01); *G01R 33/3875* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 7,078,901 B2   7/2006 Feiweier et al.
2003/0073917 A1*  4/2003 Echauz ............... A61B 5/0476
600/510
(Continued)

FOREIGN PATENT DOCUMENTS

WO   2011/033402 A1   3/2011

OTHER PUBLICATIONS

English Translation of International Preliminary Search Report, dated Feb. 12, 2015, 7 pages.
(Continued)

*Primary Examiner* — Walter L Lindsay, Jr.
*Assistant Examiner* — Frederick Wenderoth
(74) *Attorney, Agent, or Firm* — Brundidge & Stanger, P.C.

(57) ABSTRACT

With an MRI apparatus using a transmission coil having multiple channels, a region desired to be diagnosed is efficiently imaged with high image quality. The MRI apparatus comprises a region setting means for setting a region in an imaging region, of which high quality image is desired to be obtained, as a first region, and an optimization means for determining at least one of amplitude and phase of a radio frequency wave transmitted to each of the multiple channels as a radio frequency magnetic field condition, and the optimization means determines the radio frequency magnetic field condition so that at least one of specific absorption ratio and signal value of a region that generates artifacts is not higher than a predetermined value defined for each, under a uniformity constraint condition that uniformity
(Continued)

of radio frequency magnetic field distribution in the first region is not lower than a predetermined value.

4 Claims, 10 Drawing Sheets

(51) Int. Cl.
    *A61B 5/055*     (2006.01)
    *G01R 33/34*     (2006.01)
    *G01R 33/385*     (2006.01)
    *G01R 33/3875*     (2006.01)

(58) Field of Classification Search
    USPC .......................................................... 324/307
    See application file for complete search history.

(56) References Cited

U.S. PATENT DOCUMENTS

| | | | |
|---|---|---|---|
| 2003/0214294 A1 | 11/2003 | Zhu | |
| 2010/0253338 A1* | 10/2010 | Eryaman | G01R 33/285 |
| | | | 324/309 |
| 2011/0044524 A1* | 2/2011 | Wang | G01R 33/54 |
| | | | 382/131 |
| 2012/0025826 A1* | 2/2012 | Zhou | G01R 33/4833 |
| | | | 324/309 |
| 2012/0161766 A1* | 6/2012 | Harvey | G01R 33/5612 |
| | | | 324/309 |
| 2013/0165784 A1* | 6/2013 | Kim | A61B 8/5246 |
| | | | 600/441 |

OTHER PUBLICATIONS

Bob Van Den Bergen, 7 T Body MRI: B1 Shimming With Simultaneous SAR Reduction, Physics in Medicine and Biology, Sep. 7, 2007, V52 N17, P5429-5441.

P. Balchandani, et al, "Adiabatic B1 Shimming Algorithm for Multiple Channel Transmit at 7T", Proc.Intl.Soc.Mag.Reson.Med. 19 (2011), Jul. 13, 2011, p. 2907.

International Search Report from International Application No. PCT/JP13/070087 dated Aug. 20, 2013.

Tamer S. Ibrahim et al., Understanding and manipulating the RF fields at high field MRI, NMR in Biomedicine, 2009, pp. 927-936.

P. Balchandani, M.M.Khalighi, S.S.Hsieh, K. Setsompop, J.Pauly, and D.Spielman, "Adiabatic B1 Shimming Algorithm for Multiple Channel Transmit at 7T", Proc.Intl.Soc.Mag.Reson.Med.19 (2011), Jul. 13, 2011, p. 2907.

* cited by examiner

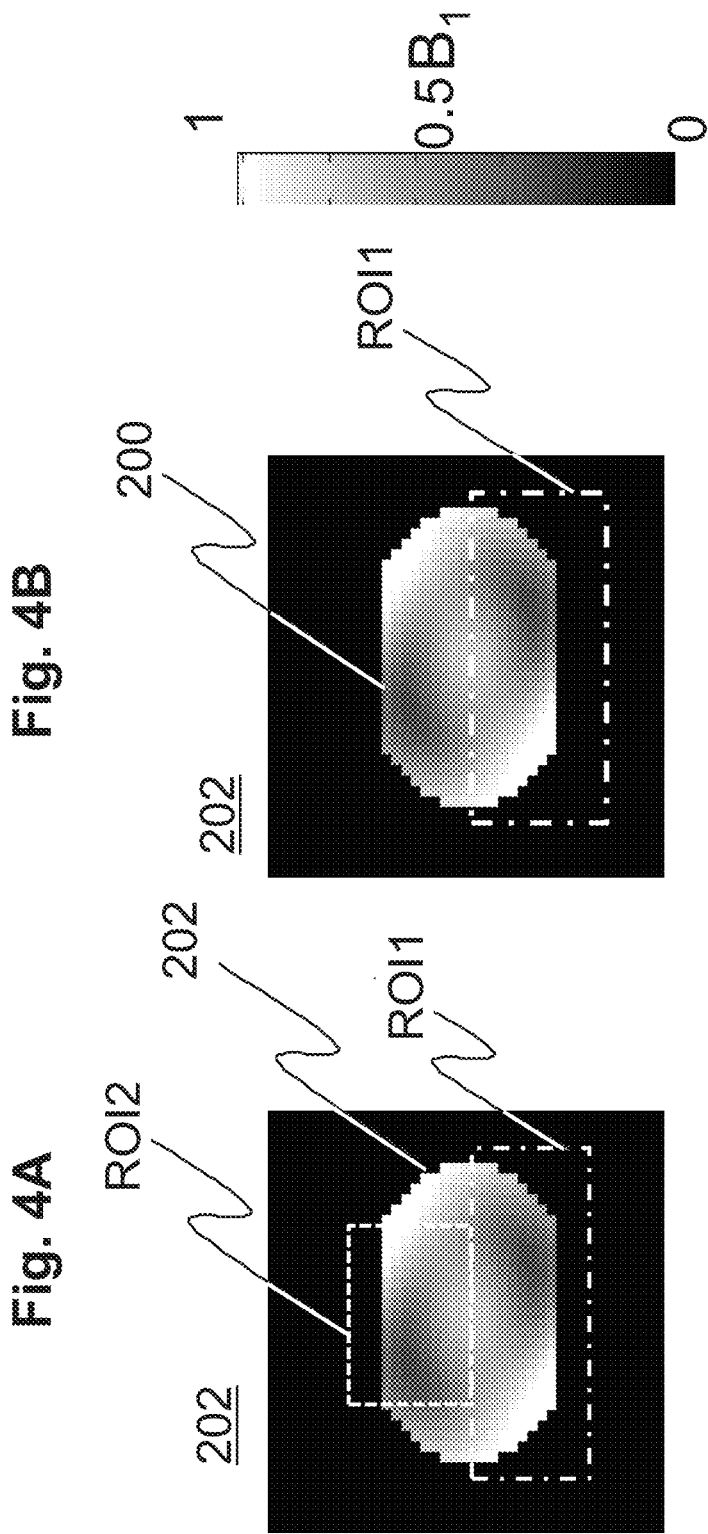

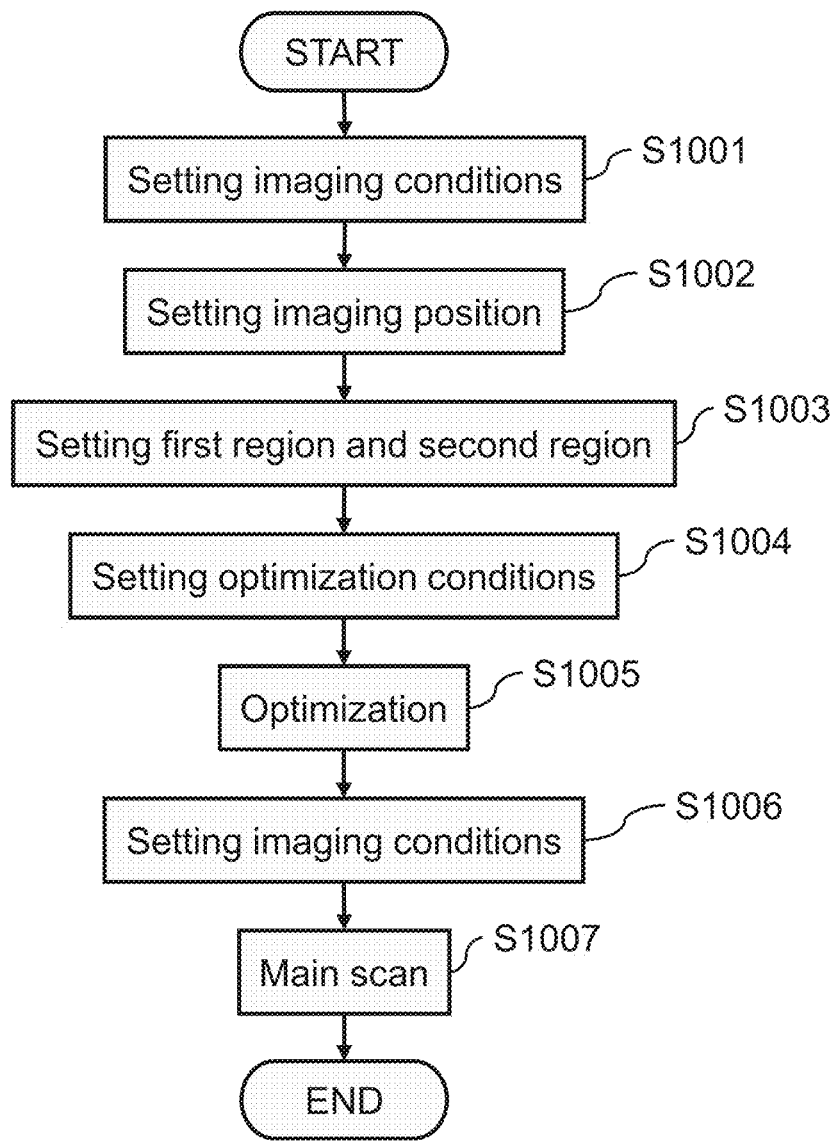

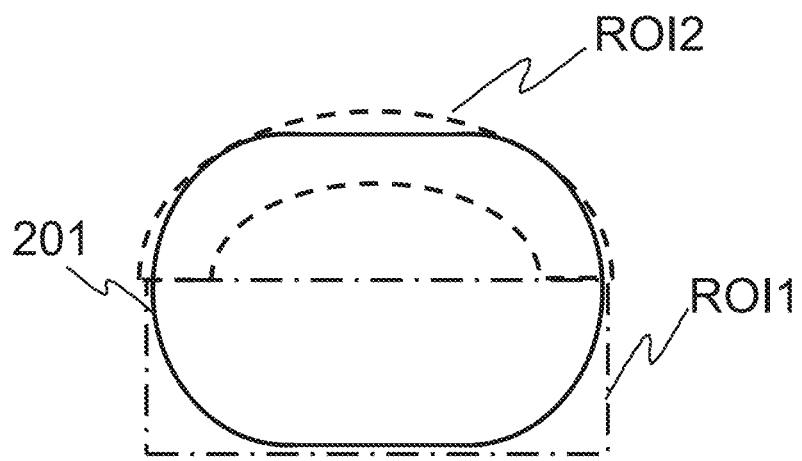

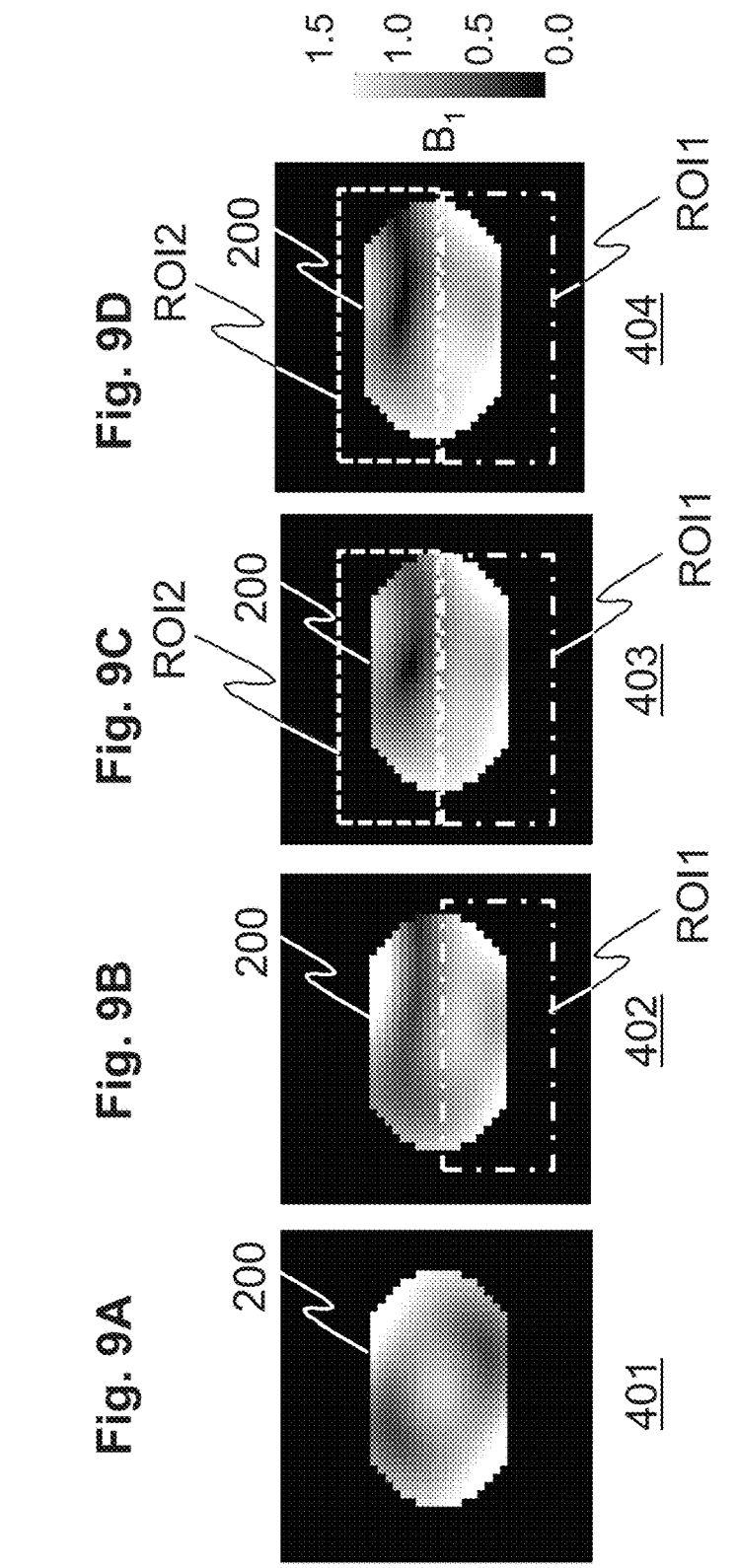

| | Case A | Case B | Case C | Case D |
|---|---|---|---|---|
| $U_{SD}$ | 0.315 | 0.115 | 0.167 | 0.167 |
| $P_{SUM}[\%]$ | 100.0 | 100.0 | 51.9 | 55.0 |
| $m_{ratio}$ | 1.00 | 0.93 | 0.52 | 0.48 |

MAGNETIC RESONANCE IMAGING DEVICE, AND DETERMINATION METHOD FOR HIGH-FREQUENCY MAGNETIC FIELD CONDITIONS

TECHNICAL FIELD

The present invention relates to a magnetic resonance imaging (MRI) technique, especially, such a technique for irradiating a radio frequency magnetic field for generating a rotating magnetic field that induces the magnetic resonance phenomenon.

BACKGROUND ART

MRI apparatuses are diagnostic imaging apparatuses for medical use, which induce magnetic resonance of atomic nuclei in an arbitrary section crossing a subject, and obtain a tomographic image of the section from generated magnetic resonance signals. They transmit a radio frequency wave (henceforth abbreviated as RF), which is a kind of electromagnetic wave, to a subject to excite spins of atomic nuclei in the subject, then receive magnetic resonance signals generated by nuclear spins, and obtain an image of the subject. RF is transmitted to the subject by a coil for RF transmission, and the magnetic resonance signals emitted by the subject are received by a coil for RF reception.

In recent years, aiming at improvement in SNR (Signal to Noise Ratio) of images, the static magnetic field intensity tends to become higher, and use of a high magnetic field MRI apparatus (super-high magnetic field MRI apparatus) using a static magnetic field intensity of 3 T (tesla) or higher has begun to spread. However, although higher static magnetic field intensity provides more improved SNR, higher static magnetic field intensity more easily produces non-uniformity in obtained images. This is because the frequency of RF used for inducing the magnetic resonance phenomenon becomes higher with use of higher magnetic field intensity. For example, for an MRI apparatus using a static magnetic field intensity of 3 T (tesla) (henceforth referred to as 3 T MRI apparatus), RF having a frequency of 128 MHz is used. In human living bodies, the wavelength of this RF is about 30 cm, which is substantially the same scale as that of a section of the abdominal part, and the phase thereof changes. This phase change makes the distribution of the irradiated RF and the spatial distribution of the rotating magnetic field for inducing the magnetic resonance phenomenon, which is generated by RF (henceforth referred to as radio frequency magnetic field distribution, $B_1$), non-uniform, and produces non-uniformity in images, as a result. Therefore, there is required a technique for reducing the non-uniformity of the distribution of the rotating magnetic field $B_1$ at the time of the RF irradiation performed by a super high magnetic field MRI apparatus.

As an RF irradiation method for reducing the non-uniformity of the $B_1$ distribution, there is a technique called "RF shimming". This is a technique for reducing the $B_1$ non-uniformity of imaging region by using a coil for transmission having multiple channels, and controlling phases and amplitudes of RF pulses applied to the channels (for example, refer to Patent document 1). In this technique, the $B_1$ distribution of each channel is measured beforehand before the main scan, and by using this $B_1$ distribution, amplitude and phase of RF pulse optimal for reducing the $B_1$ non-uniformity are calculated. In this operation, a region desired to be diagnosed is set as a region of interest (ROI), and amplitude and phase are determined so as to reduce the $B_1$ non-uniformity in the ROI.

There has also been proposed a method for irradiating RF, in which the $B_1$ value is made high only in ROI, and the $B_1$ value is made low in the other regions (for example, refer to Non-patent document 1). In this method, amplitude and phase of RF are set so that the $B_1$ value is maximized in ROI by using a ratio of $B_1$ averages of ROI and the regions other than ROI. The $B_1$ distribution is thereby locally concentrated in ROI.

Furthermore, there has also been proposed a method of highly precisely controlling the $B_1$ distribution by changing the RF waveform and gradient magnetic field waveform (for example, refer to Patent document 2).

PRIOR ART REFERENCES

Patent Documents

Patent document 1: U.S. Pat. No. 7,078,901
Patent document 2: U.S. Patent No. 2003/0214294

Non-Patent Document

Non-patent document 1: Tamer S. Ibrahim et al., Understanding and manipulating the RF fields at high field MRI, NMR in Biomedicine, 2009, pp. 927-936

SUMMARY OF THE INVENTION

Object to be Achieved by the Invention

In imaging by MRI apparatuses, artifacts generated by body motion etc. have come to more notably appear, because of the use of higher magnetic field intensity. Further, in MRI apparatuses, in consideration of safety of living bodies, the absorption ratio of RF in living bodies (SAR, Specific Absorption Ratio) is regulated to be within a predetermined range. However, with use of higher magnetic field intensity in the apparatuses, the frequency of RF to be used becomes higher, and SAR also becomes larger.

The RF shimming described in Patent document 1 or Non-patent document 1 cannot decrease artifacts and/or even SAR. Therefore, retake of image etc. are required due to artifacts, or in order to control SAR to be within a predetermined range, test procedure or imaging time may be restricted, and thus efficiency of the test is degraded. Further, the method described in Patent document 2 requires longer irradiation time of the RF pulse, thus the pulse sequence is restricted, and therefore efficiency of the test is degraded.

The present invention was accomplished in light of the aforementioned circumstances, and an object of the present invention is to provide a technique for efficiently obtaining a high quality image of a region desired to be diagnosed with an MRI apparatus using a transmission coil having multiple channels.

Means for Achieving the Object

According to the present invention, while the $B_1$ distribution in a region of interest is made to have uniformity at a level not lower than a predetermined level, at least one of SAR and artifact is reduced.

Specifically, there is provided a magnetic resonance imaging apparatus provided with a transmission coil having multiple channels each for transmitting a radio frequency wave to a subject, wherein the apparatus is provided with a region setting means for setting a region in an imaging region, of which high quality image is desired to be obtained, as a first region, and an optimization means for determining at least one of amplitude and phase of a radio frequency wave transmitted to each of the multiple channels as a radio frequency magnetic field condition, and the optimization means determines the radio frequency magnetic field condition so that uniformity of radio frequency magnetic field distribution in the first region is not lower than a predetermined value, and at least one of specific absorption ratio and signal value of a region that generates artifacts is not higher than a predetermined value defined for each.

There is also provided a method for determining radio frequency magnetic field condition by determining at least one of amplitude and phase of a radio frequency wave transmitted to each of multiple channels of a transmission coil in a magnetic resonance imaging apparatus, which are provided with a region setting step of setting a region in an imaging region, of which high quality image is desired to be obtained, as a first region, and an optimization step of determining at least one of amplitude and phase of a radio frequency wave transmitted to each of the multiple channels so that uniformity of radio frequency magnetic field distribution in the first region is not lower than a predetermined value, and at least one of specific absorption ratio and signal value of a region that generates artifacts is not higher than a predetermined value defined for each.

Effect of the Invention

According to the present invention, with an MRI apparatus using a transmission coil having multiple channels, a high quality image of a region desired to be diagnosed can be efficiently obtained.

BRIEF DESCRIPTION OF THE DRAWINGS

FIG. 4A is an explanatory drawing for explaining an example of setting of the first region and second region according to an embodiment of the present invention.

FIG. 4B is an explanatory drawing for explaining an example of setting of the first region according to an embodiment of the present invention.

FIG. 5 is a flowchart of imaging processing according to an embodiment of the present invention.

FIG. 6 is an explanatory drawing for explaining an example of setting of the first region and second region for imaging of the abdominal part according to an embodiment of the present invention.

FIG. 9A is an explanatory drawing for explaining the $B_1$ distribution in a phantom obtained without RF shimming.

FIG. 9B is an explanatory drawing for explaining the $B_1$ distribution in a phantom obtained with conventional RF shimming.

FIG. 9C is an explanatory drawing for explaining the $B_1$ distribution in a phantom obtained with the first optimization conditions according to an embodiment of the present invention.

FIG. 9D is an explanatory drawing for explaining the $B_1$ distribution in a phantom obtained with the second optimization conditions according to an embodiment of the present invention.

FIG. 10 shows examples of the index $U_{SD}$ of $B_1$ uniformity in the first region, RF irradiation power, and ratio of $B_1$ average for the first region and $B_1$ average for the second region in a phantom observed at the time of using no RF shimming, conventional RF shimming, the first optimization conditions, or the second optimization conditions, in the form of table.

MODES FOR CARRYING OUT THE INVENTION

Hereafter, embodiments of the present invention will be explained with reference to the drawings. Throughout the drawings for explaining the embodiments, the same numerals or symbols are used for components having the same function, and repetition of explanation for such components will be omitted. Further, the present invention is not limited by the following explanations.

Figure 1:
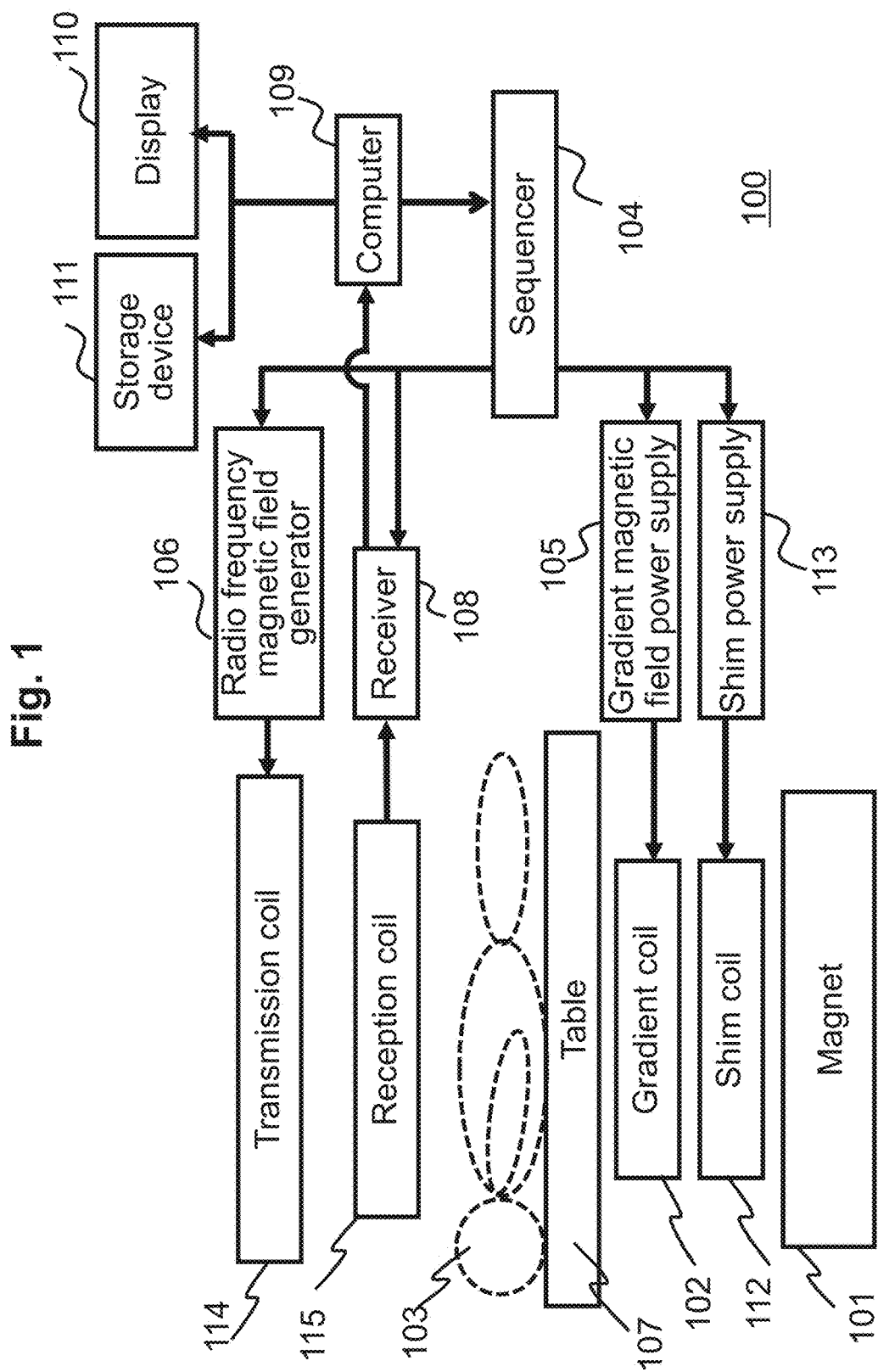
FIG. 1 is a block diagram of an MRI apparatus according to an embodiment of the present invention.

First, entire configuration of an MRI apparatus according to one embodiment will be explained. FIG. 1 is a block diagram of an MRI apparatus 100 according to this embodiment. As shown in this drawing, the MRI apparatus 100 according to this embodiment is provided with a magnet 101 for generating a static magnetic field, a coil 102 for generating a gradient magnetic field, a shim coil 112 for adjusting uniformity of static magnetic field, a sequencer 104, a coil for RF transmission (transmission coil) 114 for transmitting a radio frequency (RF) magnetic field, a coil for RF reception (reception coil) 115 for detecting (receiving) magnetic resonance signals generated from a subject 103, a table 107 for placing the subject 103, a gradient magnetic field power supply 105, a radio frequency magnetic field generator 106, a receiver 108, a shim power supply 113, and a computer 109 that controls the parts of the MRI apparatus 100 to realize imaging.

The gradient magnetic field coil 102 and the shim coil 112 are connected to the gradient magnetic field power supply 105 and the shim power supply 113, respectively. The transmission coil 114 and the reception coil 115 are connected to the radio frequency magnetic field generator 106 and the receiver 108, respectively.

The sequencer 104 sends commands to the gradient magnetic field power supply 105, the shim power supply 113, and the radio frequency magnetic field generator 106 according to the directions from the computer 109 to make them generate a gradient magnetic field and RF, respectively. RF is irradiated (transmitted) on the subject 103 via the transmission coil 114. Magnetic resonance signals generated from the subject 103 irradiated (transmitted) with RF are detected (received) by the reception coil 115, and detection is performed by the receiver 108. The magnetic resonance frequency used as the basis of the detection performed by the receiver 108 is set by the computer 109 through the sequencer 104. The detected signals are sent to the computer 109 via an A/D conversion circuit, and signal processings such as image reconstruction are performed therein. The results are displayed on a display 110 connected to the computer 109. The detected signals and measurement conditions are stored in a storage device 111 connected to the computer 109 as required.

The magnet 101, the shim coil 112, and the shim power supply 113 constitute a static magnetic field formation part for forming a static magnetic field space. The gradient coil 102 and the gradient magnetic field power supply 105 constitute a gradient magnetic field application part for applying a gradient magnetic field to the static magnetic field space. Further, the transmission coil 114 and the radio frequency magnetic field generator 106 constitute a radio frequency magnetic field transmission part for irradiating (transmitting) RF to the subject 103. The reception coil 115 and the receiver 108 constitute a signal reception part for detecting (receiving) magnetic resonance signals generated from the subject 103.

Figure 2A:
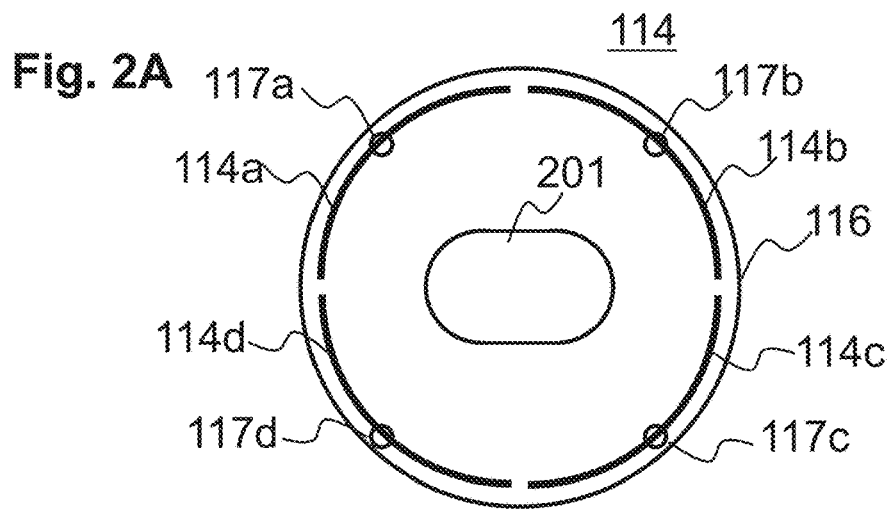
FIG. 2A is an explanatory drawing for explaining a transmission coil according to an embodiment of the present invention.

As the transmission coil 114 of this embodiment, a multi-channel coil having a plurality of channels each of which transmits unique RF. An example of the transmission coil 114 of this embodiment is shown in FIG. 2A. In this drawing, a four-channel (4-ch) coil having four of channels (114a, 114b, 114c, 114d) is shown as an example of the transmission coil 114. Amplitudes and phases of RFs transmitted to respective channels (114a, 114b, 114c, 114d) are individually and independently set by the computer 109. The radio frequency magnetic field generator 106 of this embodiment independently transmits an RF waveform to each of the channels via each of feeding points (117a, 117b, 117c, 117d) provided for the channels (114a, 114b, 114c, 114d) according to the control by the computer 109. In this drawing, the numeral 116 indicates an RF shield.

Figure 3:
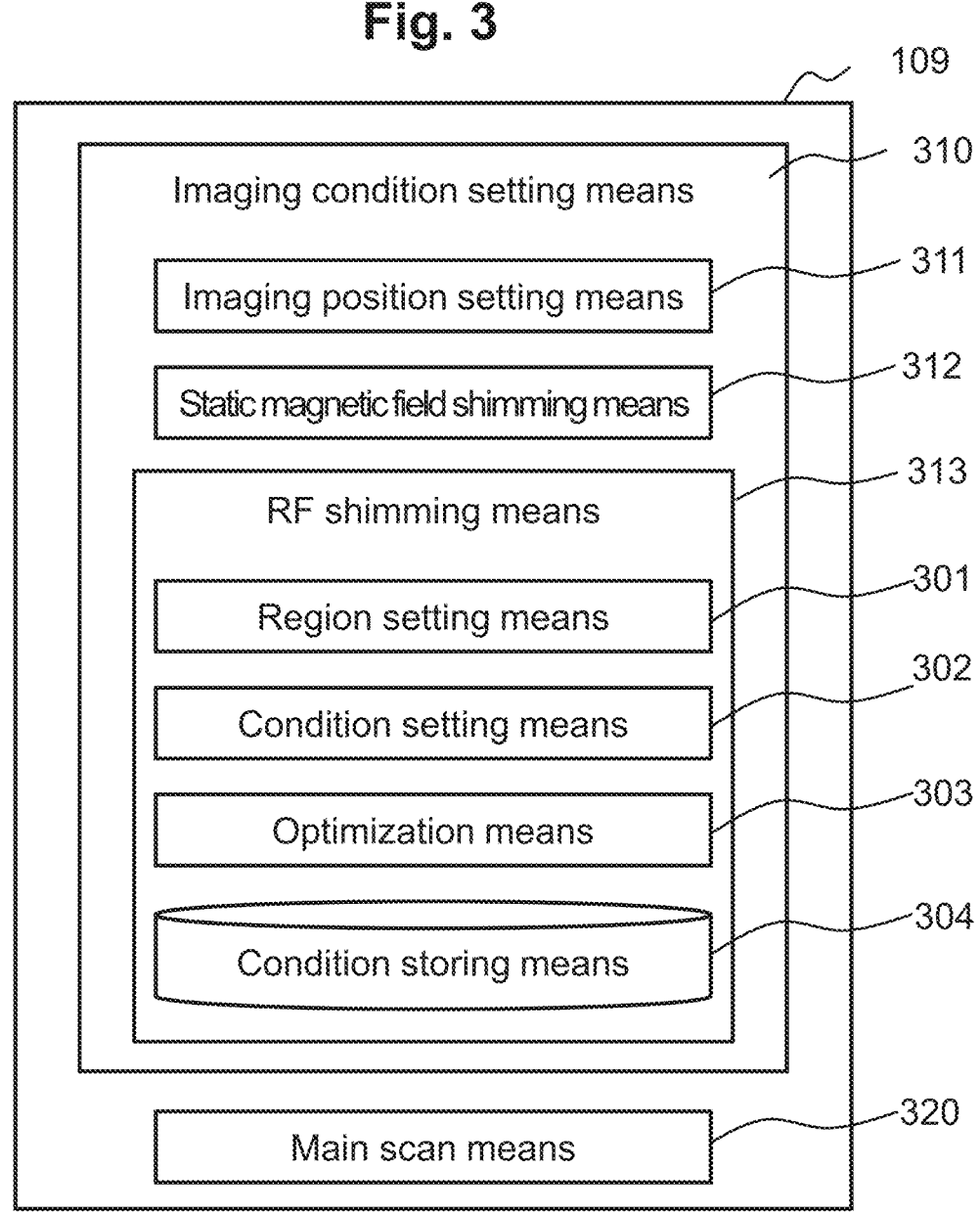
FIG. 3 is a functional block diagram of a computer according to an embodiment of the present invention.

The computer 109 used in this embodiment controls the parts involved in imaging performed by the MRI apparatus 100, so that SAR or artifact is suppressed, and a high quality image of the region of interest ROI is efficiently obtained. In order to realize such control, as shown in FIG. 3, the computer 109 of this embodiment is provided with an imaging condition setting means (imaging condition setter) 310 for setting imaging conditions, and a main scan means (main scan controller) 320 for performing main scan according to the imaging conditions set by the imaging condition setting means 310. Further, the imaging condition setting means 310 is provided with an imaging position setting means (imaging position setter) 311, a static magnetic field shimming means (static magnetic field shimming controller) 312, and an RF shimming means (RF shimming controller) 313.

The imaging position setting means 311 sets an imaging position (imaging section). A scout scan or the like is performed before the main scan is performed, and an obtained positioning image is used to set the imaging section. For example, a position is specified by a user on the positioning image displayed on the display 110, and a section at the specified position is set as the imaging section. The imaging section may be automatically set at a predetermined position defined beforehand for every part using a characteristic point or the like on the positioning image as a key. A region of the subject 103 in the imaging section is called imaging region.

The static magnetic field shimming means 312 measures the static magnetic field distribution, and adjusts the static magnetic field so that it becomes as uniform as possible. Such adjustment is performed by operating the shim coil 112 via the shim power supply 113. When adjustment of uniformity of the static magnetic field is unnecessary, the static magnetic field shimming means 312, the shim power supply 113, and the shim coil 112 may not be provided.

The RF shimming means 313 performs an RF shimming processing in which at least one of amplitude and phase of RF to be transmitted to each channel (114a, 114b, 114c, 114d) of the transmission coil 114 is determined. As described above, the RF shimming means 313 of this embodiment determines at least one of amplitude and phase of each RF so that at least one of SAR and artifact is suppressed, and a high quality image of the region of interest ROI can be efficiently obtained. At least one of amplitude and phase of each RF transmitted to each channel of the transmission coil 114, which is determined by the RF shimming means 313 of this embodiment, will be henceforth called radio frequency magnetic field condition.

In order to realize such determination as described above, the RF shimming means 313 of this embodiment is provided with a region setting means (region setter) 301, a condition setting means (condition setter) 302, an optimization means (optimization module) 303, and a condition storing means (condition storage) 304.

Figure 2B:
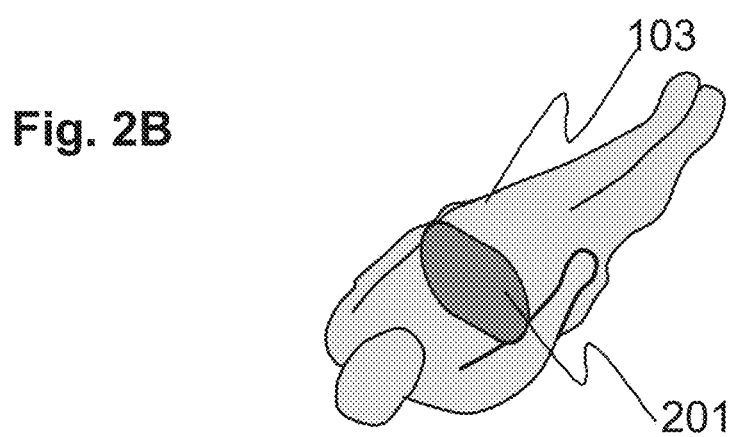
FIG. 2B is an explanatory drawing for explaining an imaging region according to an embodiment of the present invention.

In advance of explanation of the configurations of the parts for realizing the RF shimming processing of this embodiment performed by the RF shimming means 313, the method of RF irradiation performed by the transmission coil 114 of this embodiment is briefly explained. The following explanation will be made by exemplifying imaging of the abdominal part of the subject 103. At the time of imaging of the abdominal part, the imaging region 201 of the subject 103 is set as shown in FIG. 2B.

Figure 2C:
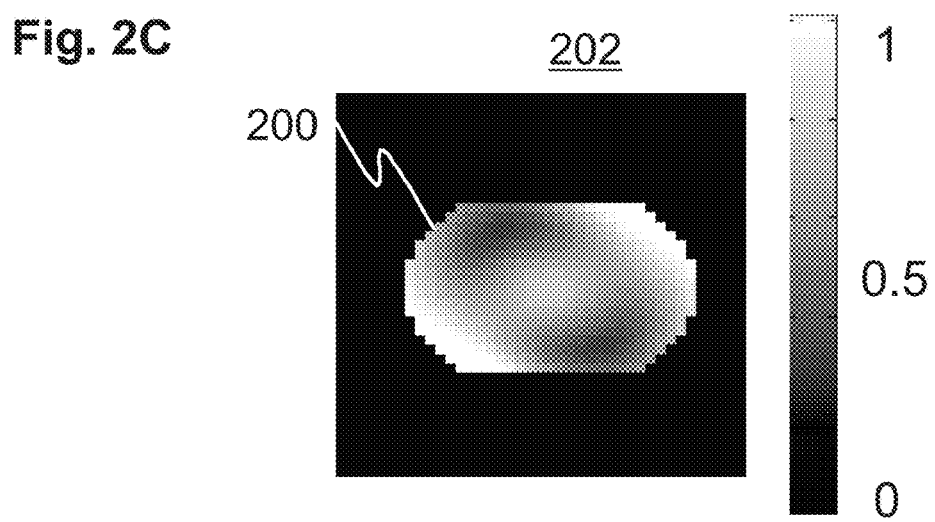
FIG. 2C is an explanatory drawing for explaining results of simulation of distribution of rotating magnetic field $B_1$ generated in a phantom according to an embodiment of the present invention.

The result of electromagnetic field simulation of the rotating magnetic field $B_1$ ($B_1$ distribution) 202 is shown in FIG. 2C, which rotating magnetic field is generated in a phantom 200 imitating the abdominal part of the subject 103, when RF is irradiated to the phantom 200 from the transmission coil 114.

In this simulation, the $B_1$ intensity within the imaging region 201 was nondimensionalized so that the maximum $B_1$ intensity in the phantom 200 became 1. The sizes of the phantom 200 in the x-, y-, and z-axis directions were 300 mm, 200 mm, and 900 mm, respectively. These sizes were determined for a simplified shape supposing a section of the abdominal part of a human living body. As for the physical properties of the phantom 200, electric conductivity was set to be 0.6 S/m, and dielectric constant was set to be 80. These values were determined by supposing a water phantom, which shows physical property values similar to those of living body. The frequency of RF to be irradiated was set to be 128 MHz, supposing a 3 T MRI apparatus.

Further, a voltage of a sine waveform represented by the following equation (1) was supplied to each feeding point (117a, 117b, 117c, 117d) of each channel (114a, 114b, 114c, 114d).

[Equation 1]

$$\begin{rcases} B\_ch1 = A1\sin(\omega t + \phi1) \\ B\_ch2 = A2\sin(\omega t + \phi2) \\ B\_ch3 = A3\sin(\omega t + \phi3) \\ B\_ch4 = A4\sin(\omega t + \phi4) \end{rcases} \quad (1)$$

A1 and φ1 represent amplitude and phase of the sine waveform voltage supplied to the feeding point 117a of the channel 114a, respectively, A2 and φ2 represent amplitude and phase of the same supplied to the feeding point 117b of the channel 114b, respectively, A3 and φ3 represent amplitude and phase of the same supplied to the feeding point 117c of the channel 114c, respectively, and A4 and φ4 represent amplitude and phase of the same supplied to the feeding point 117d of the channel 114d, respectively. Further, as for the $B_1$ distribution 202 shown in FIG. 2C, all of A1, A2, A3, and A4 were set to be 1, and the phases were set as follows: φ1=0, φ2=π/2, φ3=π, and φ4=3π/2. These values are for the RF irradiation method called quadrature drive (QD), which is a standard RF irradiation method.

When RF waveforms are transmitted from the channels (114a, 114b, 114c, 114d) with the same amplitude and phases successively differing by π/2 as in the QD irradiation, $B_1$ intensity significantly varies and becomes non-uniform in the imaging region 201 of the phantom, as shown in FIG. 2C. This is the $B_1$ non-uniformity currently considered as a problem of high magnetic field MRI apparatuses.

The RF shimming means 313 of this embodiment adjusts the amplitudes (A1, A2, A3, A4) and phases (φ1, φ2, φ3, φ4) of RFs to be transmitted to the respective channels (114a, 114b, 114c, 114d), so that the $B_1$ non-uniformity in a region especially desired to be diagnosed (diagnosis region) in the imaging region 201 is reduced, and sets optimal values thereof as the radio frequency magnetic field conditions. In this adjustment, the RF shimming means 313 of this embodiment further adjusts these parameters so that at least one of SAR and artifact is suppressed.

The RF shimming means 313 of this embodiment first specifies a diagnosis region, for which a high quality image is desired to be obtained, within the imaging region. Further, as a region that generates artifacts or increases local SAR in the diagnosis region, it specifies a suppression region. The suppression region is specified to be a region different from the diagnosis region. Then, the radio frequency magnetic field conditions are determined so that at least one of SAR and artifact is suppressed, while the $B_1$ uniformity in the diagnosis region is increased.

The region setting means 301 sets the diagnosis region and the suppression region as a first region ROI1 and a second region ROI2, respectively. This setting is performed by receiving information of regions specified by a user on the positioning image or result of $B_1$ distribution measurement performed with initial values of the radio frequency magnetic field conditions. That is, the region setting means 301 sets the first region ROI1 and the second region ROI2 according to the directions from the user. FIG. 4A shows an example of setting of the first region ROI1 and the second region ROI2 in the case of specifying the abdominal part as the imaging part.

As the region that generates artifacts, for example, a fat region or a region showing a periodic body motion such as a heart region is set. This is because intensities of signals from fat are larger than those of other tissues, and therefore the fat region more significantly contributes to generation of artifacts irrespective of the type of artifacts, i.e., periodic or random artifacts.

It may also be configured that the first region ROI1 as the diagnosis region and the second region ROI2 as the suppression region are automatically set according to the imaging part and the imaging object. In such a case, the MRI apparatus 100 is further provided with a region storing means (region storage) that memorizes candidates of the first region ROI1 and the second region ROI2 in connection with part and imaging object, and when a part and an imaging object are set as imaging conditions, the region setting means 301 extracts corresponding first region ROI1 and second region ROI2 from those stored in the region storing means in connection with the imaging part or imaging object set as the imaging conditions, and set them as the first region ROI1 and the second region ROI2. The region storing means is registered beforehand in the storage device 111.

Further, when there is no region that generates artifacts in the first region ROI1, or when artifacts are generated in such a degree that they can be ignored, even if they are generated, the second region ROI2 may not be selected, as shown in FIG. 4B.

The optimization means 303 determines at least one of amplitude (A1, A2, A3, A4) and phase (φ1, φ2, φ3, φ4) of RF transmitted to each channel (114a, 114b, 114c, 114d) as the radio frequency magnetic field conditions so that the $B_1$ distribution in the first region ROI1 is optimized. According to this embodiment, as described above, the radio frequency magnetic field conditions are determined so that value of the uniformity of the $B_1$ distribution in the first region ROI1 is not lower than a predetermined value, and at least one of SAR and artifact is reduced. According to this embodiment, this radio frequency magnetic field conditions are obtained as solutions that minimize value of an objective function defined beforehand under constraint conditions defined beforehand.

The solutions are calculated by using a method of solving an optimization problem, for example, the steepest descent method, gradient method, Newton's method, least square method, conjugate gradient method, linear programming, nonlinear programming, a method of calculating an optimal solution by comprehensively changing values of amplitude and phase, and so forth.

Further, the solutions that minimize the value of the objective function may be calculated by comprehensively changing values of amplitude and phase. For example, the values of the objective function are calculated with changing the values of amplitude and phase by 1 dB and 5 degrees, respectively, for each time of change, and amplitude and phase that minimize the value of the function are obtained. However, when enormous time is required for the calculation with comprehensively changing the amplitude and phase, for example, amplitude and phase that give the minimum value of the objective function are first obtained by changing amplitude and phase by a relatively large intervals, and then by changing amplitude and phase by smaller intervals near the obtained amplitude and phase, amplitude and phase that give the minimum value of the objective function may be obtained. The initial values of amplitude and phase for performing this calculation are stored in the storage device 111 beforehand. Further, when optimal amplitude and phase can be predicted beforehand to a certain extent, the predicted values are used as the initial values, and amplitude and phase may be comprehensively change only around the initial values.

The optimization means 303 may perform $B_1$ distribution measurement, in which the $B_1$ distribution in the imaging region is measured, whenever the radio frequency magnetic field conditions are changed, to obtain the $B_1$ value in the imaging region. Further, the radio frequency magnetic field conditions may be determined by changing only one of amplitude and phase.

The condition storing means 304 stores sets of constraint condition and objective function (optimization conditions) used by the optimization means 303 for calculation of the radio frequency magnetic field conditions. According to directions of a user, the condition setting means 302 extracts optimization conditions used by the optimization means 303 for calculation of the radio frequency magnetic field conditions from those stored in the condition storing means 304, and sets them. The optimization means 303 calculates the radio frequency magnetic field conditions by using the set optimization conditions.

In addition, it may also be configured that the optimization conditions are stored in the condition storing means 304 in connection with at least one of imaging part and purpose of imaging, and the condition setting means 302 extracts the optimization conditions from those stored in the condition storing means 304 according to the imaging part set by a user, so that the optimization conditions are automatically selected and set.

The flow of the imaging processing including the RF shimming processing of this embodiment, which is performed by those functions described above, is shown in FIG. 5. The imaging processing of this embodiment is started with a direction of a user.

First, the imaging condition setting means 310 receives input of the imaging conditions including imaging parameters, imaging part, imaging object, etc. by a user and sets them (Step S1001). Then, the imaging position setting means 311 carries out a scout scan, and sets an imaging position (Step S1002). Then, the region setting means 301 sets the first region ROI1 and the second region ROI2 (Step S1003). As described above, the second region ROI2 may not be set.

Then, the condition setting means 302 extracts the optimization conditions having a set of an objective function and constraint condition from those stored in the condition storing means 304, and sets them (Step S1004). The optimization means 303 performs optimization, in which solutions that minimize the value of the objective function are calculated under the constraint condition set by the condition setting means 302 (Step S1005). Then, the imaging condition setting means 310 sets the calculated solutions as amplitude and phase of RF transmitted to each channel used for imaging as imaging conditions together with other imaging parameters (Step S1006).

Then, the main scan means 320 performs the main scan according to the imaging conditions set by the imaging condition setting means 310 (Step S1007).

The functions realized by the computer 109 are realized by CPU of the computer 109 by loading programs stored in the storage device 111 beforehand to a memory and executing them. Further, the condition storing means 304 is constructed on the storage device 111.

Hereafter, specific examples of the optimization conditions (set of objective function and constraint condition) stored by the condition storing means 304 of this embodiment will be explained. According to this embodiment, any of the uniformity of the $B_1$ distribution in the region of interest ROI, irradiation power that affects SAR, $B_1$ average in the region of interest ROI, and $B_1$ average in a region that generates artifacts in the region of interest is used for the objective function and the constraint condition according to the imaging part and object.

In the following explanations of this embodiment, the $B_1$ distribution uniformity index $U_{SD}$ represented by the following equation (2) is used as an index representing uniformity of the $B_1$ distribution in the imaging region 201. The $B_1$ distribution uniformity index $U_{SD}$ is a value obtained by dividing the standard deviation of the $B_1$ value with the $B_1$ average. A smaller $B_1$ distribution uniformity index $U_{SD}$ represents higher uniformity of the $B_1$ distribution in the objective region.

[Equation 2]

$$U_{SD} = \frac{\sigma(B_1)}{m(B_1)} \qquad (2)$$

First, the first optimization conditions will be explained. In the first optimization conditions, an index that specifies irradiation powers of RFs transmitted to the channels of the transmission coil 114 is used as the objective function. Specifically, an irradiation power index $P_{SUM}$ represented by the following equation (3) is used. The irradiation power index $P_{SUM}$ corresponds to the sum of squares of amplitudes of RFs transmitted to the channels.

[Equation 3]

$$P_{SUM} = A1^2 + A2^2 + A3^2 + A4^2 \qquad (3)$$

Further, as the constraint condition, it is defined that the $B_1$ distribution uniformity index $U_{SD\_ROI1}$ of the first region ROI1 is not larger than a predetermined value $U_U$. As this predetermined value $U_U$, a value that can realize predetermined image quality is defined beforehand, and is stored in the condition storing means 304 together with the optimization conditions. The constraint condition that the $B_1$ distribution uniformity index $U_{SD\_ROI1}$ of the first region ROI1 is not larger than the predetermined value $U_U$ is referred to as uniformity constraint condition.

Therefore, if the first optimization conditions are set by the condition setting means 302 as the optimization conditions, the optimization means 303 calculates the radio frequency magnetic field conditions as the optimal solutions of the following equation (4).

[Equation 4]

$$\left. \begin{array}{l} \min(P_{SUM}) \\ \text{subject to } U_{SD\_ROI1} \leq U_U \end{array} \right\} \qquad (4)$$

If the first optimization conditions are chosen, and the radio frequency magnetic field conditions are determined, the $B_1$ distribution uniformity index $U_{SD}$ of the first region ROI1 as the diagnosis region is suppressed according to the uniformity constraint condition to be not larger than a predetermined value. Therefore, the first region ROI1 comes to have uniformity not lower than a predetermined level. Further, the power $P_{SUM}$ of RFs irradiated from the channels is minimized. Therefore, the irradiation power for the whole imaging region 201 is minimized, and SAR can be suppressed.

In particular, when regions other than the diagnosis region are regions that do not generate artifacts, SAR can be effectively suppressed with maintaining the image quality of the diagnosis region. In such a case, the second region ROI2 may not be selected.

Hereafter, second optimization conditions will be explained. In the second optimization conditions, a ratio $m_{ratio}$ of the $B_1$ average of the second region ROI2, mean($B_{1\_ROI2}$), to the $B_1$ average of the first region ROI1, mean($B_{1\_ROI1}$), represented by the following equation (5) is used as the objective function. The ratio $m_{ratio}$ is a value obtained by dividing the $B_1$ average of the second region ROI2, mean($B_{1\_ROI2}$), with the $B_1$ average of the first region ROI1 mean($B_{1\_ROI1}$), as shown in the equation (5). The ratio $m_{ratio}$ will be henceforth referred to as $B_1$ ratio.

[Equation 5]

$$m_{ratio} = \frac{\text{mean}(B_{1\_ROI2})}{\text{mean}(B_{1\_ROI1})} \quad (5)$$

Further, as the constraint condition, two kinds of conditions, the aforementioned uniformity constraint condition, and the irradiation power constraint condition that the irradiation power index $P_{SUM}$ of the imaging region is not larger than a predetermined value $P_U$, are used. The predetermined value $P_U$ used for the irradiation power constraint condition is defined beforehand from the viewpoints of safety etc., and is stored in the condition storing means 304 together with the optimization conditions.

Therefore, if the second optimization conditions are set by the condition setting means 302 as the optimization conditions, the optimization means 303 calculates the radio frequency magnetic field conditions as the optimal solutions of the following equation (6).

[Equation 6]

$$\min(m_{ratio}) \\ \text{subject to } \begin{Bmatrix} P_{SUM} \leq P_U \\ U_{SD\_ROI1} \leq U_U \end{Bmatrix} \quad (6)$$

$B_1$ represents sensitivity for each region. By relatively suppressing the sensitivity for the suppression region, the signal intensity of the suppression region is relatively reduced with respect to the signal intensity of the diagnosis region. Therefore, if the second optimization conditions are chosen, and the radio frequency magnetic field conditions are determined, the $B_1$ ratio is minimized, therefore signals from the second region ROI2 can be suppressed, and signals from the first region ROI1 can be relatively enhanced. Further, the $B_1$ distribution uniformity of the first region ROI1 and the irradiation power for the imaging region 201 are suppressed to be not higher than predetermined values, respectively. Therefore, the image of the diagnosis region can be obtained with high image quality, and SAR can also be suppressed. Further, since the signal value of the suppression region can be suppressed, artifacts of the diagnosis region can be reduced, and an image of higher quality can be obtained.

In particular, if the second optimization conditions are used, SAR can be effectively suppressed with maintaining image quality of the diagnosis region for a diagnosis object that is a part close to a part that easily generates artifacts.

Therefore, for example, the second optimization conditions may be stored in the condition storing means 304 as those corresponding to the abdominal part as the imaging part. As described above, signal intensity of fat is larger than those of other tissues, and therefore signals from fat significantly contribute to motion artifacts. Therefore, when imaging of the abdominal part is performed, by setting a region of an upper part of the abdominal part, in which a large amount of fat exists (fat region), as the second region ROI2, and determining the radio frequency magnetic field conditions according to the second optimization conditions, the signal values of the fat region can be made small, and artifacts can be reduced.

In such a case, by choosing the fat region with good precision, and setting it as the second region ROI2, the $B_1$ ratio of the fat region can be more effectively reduced. An example of setting of the first region ROI1 and the second region ROI2 in the case of imaging of the abdominal part is shown in FIG. 6. The surface of the upper abdominal part constitutes a region in which a large amount of fat exists. Therefore, a region of the surface of the upper abdominal part is set as the second region ROI2. By limiting the range of the second region ROI2 with good precision as described above, signal values can be effectively reduced only for a region of which signal values are desired to be reduced. As for the method of selecting the fat region, a user may specify a fat region by using an image in which water and fat are separated, or a computer may automatically specify a fat region.

Hereafter, third optimization conditions will be explained. In the third optimizations, the $B_1$ ratio represented by the aforementioned equation (6) is used as the objective function. Further, as the constraint conditions, the uniformity constraint condition, and a first region magnetic field constraint condition that the $B_1$ average of the first region ROI1, mean($B_{1\_ROI1}$), is not lower than a predetermined value $B_L$ are used. The predetermined value $B_L$ used in the first region magnetic field constraint condition is defined beforehand, and is stored in the condition storing means 304 together with the optimization conditions.

Therefore, if the third optimization conditions are set as the optimization conditions by the condition setting means 302, the optimization means 303 calculates the radio frequency magnetic field conditions as solutions of the following equation (7).

[Equation 7]

$$\min(m_{ratio}) \\ \text{subject to } \begin{Bmatrix} U_{SD\_ROI1} \leq U_U \\ \text{mean } B_{1\_ROI1} \geq B_L \end{Bmatrix} \quad (7)$$

If the third optimization conditions are chosen, and the radio frequency magnetic field conditions are determined, the $B_1$ ratio is minimized under the condition that the $B_1$ average is not smaller than the predetermined value, and therefore the signal values of the second region ROI2 can be relatively suppressed with maintaining the signal values in the first region ROI1 to be not lower than the predetermined value. Therefore, artifacts can be effectively suppressed. Further, since the $B_1$ distribution uniformity of the first region ROI1 is maintained to be not lower than the predetermined level, the region of which diagnosis is desired is imaged with high image quality.

As for the third optimization conditions, for example, when a region that more easily generates artifacts due to periodic body motion is included outside the diagnosis region of the imaging region 201, the part of the periodic body motion can be set as the second region ROI2, and the conditions can be applied. Therefore, the third optimization conditions may be stored in the condition storing means 304, for example, as those corresponding to the breast as the imaging part. This is because the heart that shows periodic body motions is included in the imaging region at the time of imaging of the breast.

Figure 7A:
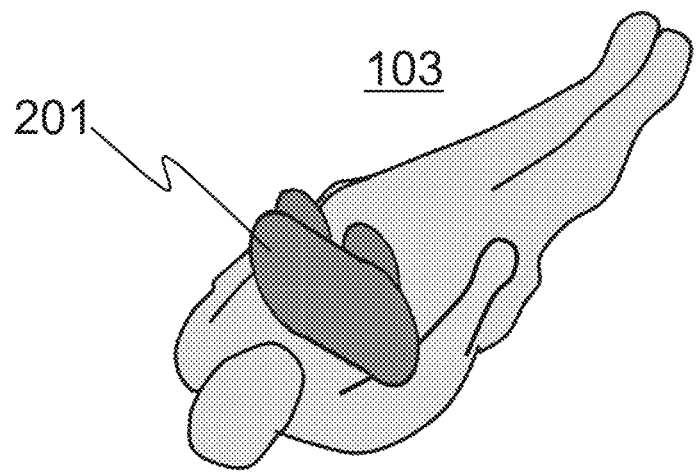
FIG. 7A is an explanatory drawing for explaining an imaging region for imaging of the breast according to an embodiment of the present invention.
Figure 7B:
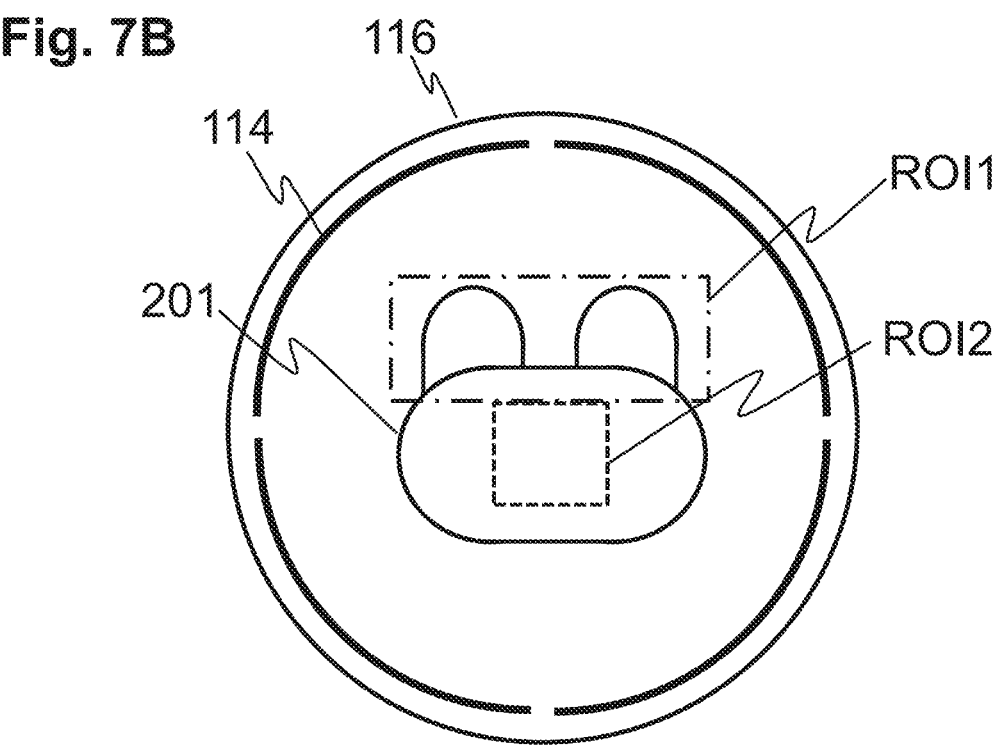
FIG. 7B is an explanatory drawing for explaining an example of setting of the first region and second region for imaging of the breast according to an embodiment of the present invention.

FIG. 7A is a drawing for explaining the imaging region 201 at the time of imaging of the breast. The imaging region 201 is specified by the imaging position (imaging section) set by the imaging position setting means 311. Further, FIG. 7B is an explanatory drawing for explaining the first region ROI1 and second region ROI2 set by the region setting means 301 in the above case. As shown in this drawing, a region of the breast is set as the first region ROI1, and a region of the heart is set as the second region ROI2.

By transmitting RFs each having the amplitude and phase calculated according to the aforementioned third optimization conditions from the channels, the $B_1$ uniformity of the region of the breast (first region ROI1) is improved, and signal values not lower than a predetermined level are acquired. On the other hand, the signal values of the heart region (second region ROI2) can be suppressed. Therefore, an image of high quality in which artifacts of the breast region are reduced can be obtained.

Hereafter, fourth optimization conditions will be explained. In the fourth optimization conditions, the reciprocal of the $B_1$ average of the first region ROI1 (1/mean $(B_{1\_ROI1})$) is used as the objective function. Further, as the constraint conditions, the uniformity constraint condition, and a second region magnetic field constraint condition that the $B_1$ average of the second region ROI2, mean($B_{1\_ROI2}$), is not larger than the predetermined value $B_U$, are used.

Therefore, if the fourth optimization conditions are set as the optimization conditions by the condition setting means 302, the optimization means 303 calculates the radio frequency magnetic field conditions as solutions of the following equation (8).

[Equation 8]

$$\min\left(\frac{1}{\text{mean}(B_{1\_ROI1})}\right) \quad \text{subject to} \begin{cases} U_{SD\_ROI1} \le U_U \\ \text{mean}(B_{1\_ROI2}) \le U_U \end{cases} \quad (8)$$

According to the fourth optimization conditions, the radio frequency magnetic field conditions are determined so that the $B_1$ average is maximized for the diagnosis region (first region ROI1) under the condition that the value of the uniformity of the $B_1$ distribution is not smaller than a predetermined value. Further, as for the suppression region (second region ROI2), the radio frequency magnetic field conditions are determined so that the $B_1$ average is not larger than a predetermined value. Therefore, the signal values of the suppression region are suppressed, artifacts are reduced, and image quality for the diagnosis region is improved. In addition, the objective function used in this case is not limited to the aforementioned function. Any function with which artifacts are reduced may be used.

The fourth optimization conditions can be used for, for example, the off-center imaging, in which the center of the subject 103 deviates from the center of the magnetic field. Therefore, the fourth optimization conditions may be stored in the condition storing means 304, for example, as those corresponding to the shoulder as an imaging part.

Figure 8A:
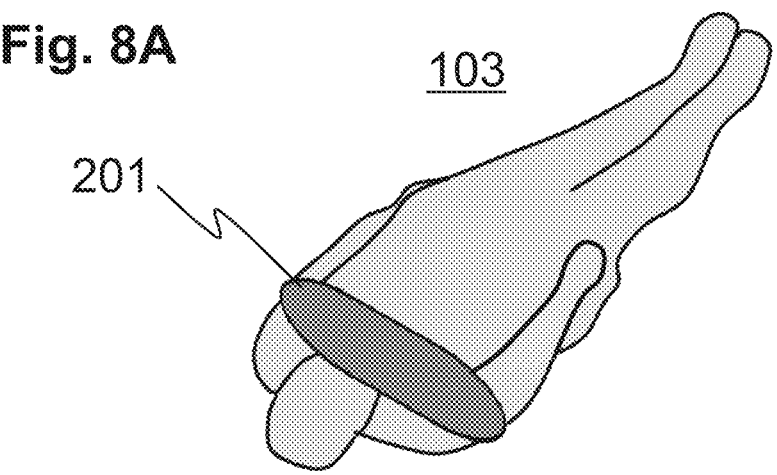
FIG. 8A is an explanatory drawing for explaining an imaging region for imaging of the shoulder according to an embodiment of the present invention.
Figure 8B:
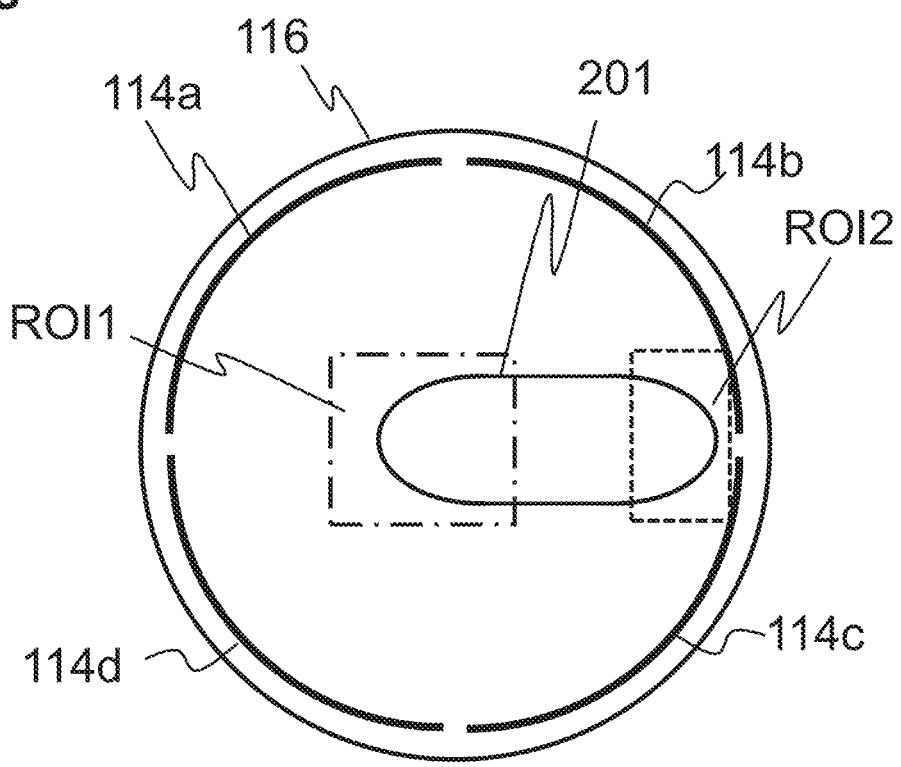
FIG. 8B is an explanatory drawing for explaining an example of setting of the first region and second region for imaging of the shoulder according to an embodiment of the present invention.

FIG. 8A is a drawing for explaining the imaging region 201 at the time of imaging of the shoulder. The imaging region 201 is specified by the imaging position (imaging section) set by the imaging position setting means 311. Further, FIG. 8B is an explanatory drawing for explaining the first region ROI1 and second region ROI2 set by the region setting means 301 in the above case. As shown in this drawing, a region of the shoulder as the object of imaging is set as the first region ROI1, and a region of the other shoulder is set as the second region ROI2.

For imaging of the shoulder, the off-center imaging is performed, in which the subject 103 is placed so that the shoulder as the object of the imaging is located at the center of the transmission coil 114 (magnetic field center) as described above, in order to image the shoulder as the object of imaging with high image quality. Therefore, as shown in FIG. 8B, the region of the shoulder that is not the object of the imaging locates near the transmission coil 114, and local SAR tends to become high.

Therefore, the fifth optimization conditions using the uniformity constraint condition and a local power constraint condition that the irradiation power of RF transmitted from a channel near the region of which local SAR is desired to be reduced, i.e., a channel near the second region, is not higher than a predetermined value, as the constraint conditions of the optimization conditions aiming at reduction of local SAR, may be stored as those corresponding to the shoulder. In such a case, the objective function is the same as that for the fourth optimization conditions.

For example, when the channel 114b and the channel 114c are channels near the region of which local SAR is desired to be reduced as shown in FIG. 8B, the sum of the irradiation powers of these channels ($A_2^2+A_3^2$) is made to be not higher than a predetermined value $A_U$. This predetermined value $A_U$ is defined beforehand, and stored in the condition storing means 304 together with the optimization conditions.

Therefore, in the above case, if the fifth optimization conditions are set by the condition setting means 302 as the optimization conditions, the optimization means 303 determines amplitude and phase of RF transmitted to each channel as solutions of the following equation (9).

[Equation 9]

$$\min\left(\frac{1}{\text{mean}(B_{1\_ROI1})}\right) \quad \text{subject to} \begin{cases} U_{SD\_ROI1} \le U_U \\ A2^2 + A3^2 \le A_U \end{cases} \quad (9)$$

Further, the sixth optimization conditions using the sum of irradiation powers of RFs transmitted from channels near the region of which local SAR is desired to be reduced (second region ROI2) as the objective function, and using the uniformity constraint condition and an SAR constraint condition that SAR of the second region ROI2 ($SAR_{ROI2}$) is not larger than the predetermined value $SAR_U$ as the constraint conditions may be stored as those corresponding to the shoulder. The predetermined value $SAR_U$ used in the SAR constraint condition is defined beforehand, and is stored in the condition storing means 304 together with the optimization conditions.

Therefore, for example, if the channel 114b and the channel 114c are the channels near the region for which reduction of local SAR is desired, the optimization means 303 determines the radio frequency magnetic field conditions as solutions of the following equation (10), in this case.

[Equation 10]

$$\min(A2^2 + A3^2) \\ \text{subject to } \begin{Bmatrix} U_{SD\_ROI1} \le U_U \\ SAR_{ROI2} \le SAR_U \end{Bmatrix} \quad (10)$$

In this case, SAR of the second region ROI2 is estimated from, for example, the $B_1$ distribution. Further, it may be calculated by electromagnetic field simulation. When it is calculated by electromagnetic field simulation, such a method as a method of using calculation results of SAR distribution in a human body model may be used.

A region of the shoulder as the object of imaging is set as the first region ROI1, and a region of the other shoulder near the transmission coil 114 is set as the second region ROI2. After such setting, by transmitting RFs having amplitudes and phases calculated according to the aforementioned fifth or sixth optimization conditions from the channels, while the $B_1$ uniformity in the region of the shoulder as the object of imaging (first region ROI1) is maintained to be at a predetermined level, the irradiation power for the region near the other shoulder (second region ROI2) can be suppressed.

Therefore, if the fifth or sixth optimization conditions are chosen, and the radio frequency magnetic field conditions are determined, the $B_1$ uniformity of the diagnosis region is made not smaller than the predetermined value, and the irradiation power for the region near the suppression region is suppressed. Therefore, the image quality of the diagnosis region is improved, and local SAR is reduced.

Hereafter, seventh optimization conditions will be explained. In the seventh optimization conditions, an index combining weighted irradiation power index $P_{SUM}$ represented by the following equation (11) and $B_1$ ratio is used as the objective function. This index is henceforth referred to as synthetic index.

[Equation 11]

$$\alpha P_{SUM} + \beta m_{ratio} \quad (11)$$

As for α and β mentioned in the equation, it is defined that α+β=1. Further, the values of α and β are determined by a user depending on which one of α and β is considered more important. Alternatively, they may be determined beforehand for each imaging part. As the constraint condition, the uniformity constraint condition is used.

Therefore, if the seventh optimization conditions are set as the optimization conditions by the condition setting means 302, the optimization means 303 calculates the radio frequency magnetic field conditions as optimal solutions of the following equation (12).

[Equation 12]

$$\min(\alpha P_{SUM} + \beta m_{ratio}) \\ \text{subject to } U_{SD\_ROI1} \le U_U \quad (12)$$

If the seventh optimization conditions are chosen, and the radio frequency magnetic field conditions are determined, the effects obtained at the times of choosing the first optimization conditions and the second optimization conditions are obtained. Further, degree of the effects can be controlled with the coefficients to be set.

The optimization conditions stored in the condition storing means 304 are not limited to the aforementioned seven kinds of optimization conditions. The optimization conditions may be such conditions that the uniformity of the $B_1$ distribution in the first region ROI1 as the diagnosis region is made to be not lower than a predetermined level, and solutions that can realize at least one of effective reduction of artifacts and suppression of SAR can be obtained. Further, they may be such conditions that at least one of the level of artifacts and the level of SAR is made to be not higher than a predetermined level, and solutions that can realize improvement in the uniformity of the $B_1$ distribution in the first region ROI1 can be obtained.

Hereafter, the simulation results of the RF shimming according to this embodiment will be shown in contrast to those obtained by the conventional RF shimming and without RF shimming.

There will be shown here the results of electromagnetic field simulation of the rotating magnetic field $B_1$ generated within the phantom 200 imitating the subject 103 at the time of irradiating RF to the phantom 200. For the simulation, the RF coil having four channels shown in FIG. 2A is used as the transmission coil 114. The specification of the phantom 200 used is the same as that used for the electromagnetic field simulation of which result is shown in FIG. 2C. Further, the frequency of the irradiated RFs was similarly 128 MHz. The sine waveform of the electric power supplied to the feeding points (117a, 117b, 117c, 117d) was also the same.

FIG. 9A shows the $B_1$ distribution 401 obtained without RF shimming, i.e., obtained by using the set initial values of amplitude and phase of RFs transmitted to the channels as they are (case A).

FIG. 9B shows the $B_1$ distribution 402 obtained by performing the conventional RF shimming, i.e., obtained by optimizing amplitude and phase of each RF so that the $B_1$ distribution in the first region ROI1 is made uniform (case B). As the index of the $B_1$ uniformity, $U_{SD}$ represented by the aforementioned equation (2) was used.

FIG. 9C shows the $B_1$ distribution 403 obtained by optimizing amplitude and phase of each RF using the first optimization conditions of this embodiment as the optimization conditions (case C), and FIG. 9D shows the $B_1$ distribution 404 obtained by optimizing amplitude and phase of each RF using the second optimization conditions of this embodiment as the optimization conditions (case D).

In the simulation of which results are shown in FIG. 9, nondimensionalization was performed so that the maximum $B_1$ intensity in the phantom 200 shown in FIG. 9A became 1, as in the simulation of which results are shown in FIG. 2C.

Further, in Table 500 of FIG. 10, there are shown values of the $B_1$ uniformity index $U_{SD}$, RF irradiation power $P_{SUM}$, and $B_1$ ratio $m_{ratio}$ for the first region ROI1 in the phantom 200 observed with each of the four kinds of the RF irradiation methods of which results are shown in FIGS. 9A to 9D. The RF irradiation power $P_{SUM}$ in the case of not performing RF shimming (case A) of which results are shown in FIG. 9A was taken to be 100% as the standard. The $B_1$ ratio was the ratio of the $B_1$ average in the first region ROI1 and the $B_1$ average in the region outside the first region ROI1. Since the $B_1$ distribution was symmetric for the starting point, $B_1$ ratio was 1.

As shown in FIG. 9B, the most uniform $B_1$ distribution in the first region ROI1 was obtained with the conventional RF shimming. However, $B_1$ of the region outside the first region ROI1 could not be controlled by the conventional RF shimming.

On the other hand, it can be seen that, as shown in FIG. 9C, when the RF shimming was performed according to the first optimization conditions of this embodiment, $B_1$ of the upper part of the phantom 200 was suppressed to be low compared with $B_1$ of the lower part of the phantom. Further, it can be seen that, as shown in FIG. 9D, when the RF shimming was performed according to the second optimization conditions of this embodiment, $B_1$ of the upper part of the phantom 200 was suppressed to be low compared with $B_1$ of the lower part of the phantom 200.

Further, as shown in Table 500 of FIG. 10, if the result obtained without RF shimming (case A) is used as the standard, when the conventional RF shimming was used (case B), $U_{SD}$ became small, and the $B_1$ distribution in the first region ROI1 became uniform. However, the RF irradiation power $P_{SUM}$ was not different from that of the case not using RF shimming (case A).

In the case of using the RF shimming according to the first optimization conditions (case C), $U_{SD}$ becomes smaller, and the RF irradiation power became 51.9%, compared with those obtained in the case of not using RF shimming (case A). Therefore, it can be seen that the $B_1$ uniformity was improved, and the total SAR (SAR absorbed by the whole living body) was reduced by the RF shimming according to the first optimization conditions.

As described above, under the first optimization conditions, $U_{SD}$ in the first region ROI1 is set to be such a value ($U_U$) that image quality higher than a predetermined level can be realized under the constraint condition, or smaller. Therefore, by performing the RF shimming according to the first optimization conditions, it becomes possible to obtain $B_1$ uniformity that can realize image quality higher than a predetermined level, and reduce SAR by half. In this case, the value of $U_{SD}$ (0.167) at the time of performing RF shimming with two channels was used as $U_U$. That is, it was demonstrated that SAR can be reduced by half with realizing $B_1$ uniformity obtainable by using two channels by controlling the RF parameters for the four channels.

In the case of using the RF shimming according to the second optimization conditions (case D), $U_{SD}$ became smaller compared with that observed in the case of not using RF shimming (case A), and further, the $B_1$ ratio $m_{ratio}$ became smallest. When the $B_1$ average of the first region ROI1 was defined to be 1, the $B_1$ average in the second region ROI2 was 0.48, and thus it can be seen that the $B_1$ value of the upper part of the phantom 200 set as the second region ROI2 was reduced. It is thereby made possible to suppress artifacts produced in the upper part of the phantom 200.

As explained above, the MRI apparatus 100 of this embodiment is an MRI apparatus 100 provided with a transmission coil having multiple channels each for transmitting a radio frequency wave to a subject, which is provided with the region setting means 301 for setting a region in an imaging region, for which a high quality image is desired to be obtained, as the first region, and the optimization means 303 for determining at least one of amplitude and phase of the radio frequency wave transmitted to each of the multiple channels as the radio frequency magnetic field condition, and wherein the optimization means 303 determines the radio frequency magnetic field condition so that uniformity of radio frequency magnetic field distribution in the first region becomes not lower than a predetermined level, and at least one of specific absorption ratio and signal value of a region that generates artifacts becomes not higher than a predetermined value defined for each.

The optimization means 303 may preliminarily choose at least one of the aforementioned uniformity, specific absorption ratio, and signal value of a region that generates artifacts for the constraint condition, and at least one of the remainder for the objective function, calculate and determines the radio frequency magnetic field conditions as solutions that optimize the objective function. Further, the aforementioned region setting means 301 may further set a region in the imaging region other than the first region, which is a region including a region that generates artifacts or a region that shows high specific absorption ratio, as the second region.

As described above, according to this embodiment, the $B_1$ distribution uniformity index $U_{SD}$ of the first region ROI1, which is a region desired to be diagnosed, is suppressed to be not higher than a predetermined value. Therefore, the first region ROI1 can maintain a predetermined $B_1$ uniformity. Further, according to the optimization conditions, the power $P_{SUM}$ of RFs irradiated from the channels is minimized or suppressed to be not higher than a predetermined value. Thus, SAR can be suppressed. Further, for example, depending on the purpose, a region outside the diagnosis region is set as the second region ROI2, and $B_1$ value or irradiation power of this region is reduced. For example, if a region that significantly contributes to the generation of artifacts is set as the second region ROI2, and $B_1$ value thereof is reduced, artifacts can be efficiently reduced. Further, if a region that locally generates high SAR is set as the second region ROI2, and the irradiation power for it is reduced, local SAR can be efficiently reduced.

Therefore, according to this embodiment, the irradiation RF parameters that enable imaging of a region desired to be diagnosed with high image quality, and reduce at least one of SAR and artifacts can be determined. Further, since imaging is performed with these parameters, a high quality image of the region desired to be diagnosed can be efficiently obtained.

In the explanation of the aforementioned embodiment, a solution that minimizes each objective function is calculated in the optimization processing. However, the present invention is not limited to such an embodiment. For example, a reciprocal of each objective function mentioned above is set as each objective function, and a solution that maximizes it may be calculated. Furthermore, it may also be configured so that each index is multiplied with −1, and a solution that maximizes the obtained index is calculated.

Further, the aforementioned embodiment may be used together with application of a presaturation pulse, which is used for reducing artifacts. For example, as shown in FIG. 9D, when the lower half region (first region ROI1) of the section is uniformly irradiated, and signal of the upper half region (second region ROI2) is suppressed as much as possible, a presaturation pulse is irradiated to the upper half region.

By irradiating the presaturation pulse to the upper half region, which is the objective region of the irradiation, as uniformly as possible, higher artifact-reducing effect is obtained. For this reason, when a presaturation pulse is irradiated, it is desirable to calculate the RF parameters so that the $B_1$ distribution of the upper half region becomes as uniform as possible. That is, if the $B_1$ uniformity of the second region ROI2 is represented as $U_{SD\_ROI2}$, the objective function is set as the following equation (13), and the RF parameters for the presaturation pulse are calculated.

[Equation 13]

$$\min(U_{SD\_ROI2}) \quad (13)$$

Then, after application of the presaturation pulse, an excitation pulse is irradiated with such RF parameters that the $B_1$ distribution of the lower half region (first region ROI1) becomes uniform as described above. By using optimal RF parameters for each of the presaturation pulse and excitation pulse as described above, higher artifact-reducing effect can be obtained.

Although the aforementioned embodiment is explained by exemplifying a case where one first region ROI1 as the diagnosis region and one second region ROI2 as the suppression region are set, the present invention is not limited to such an embodiment. Two or more regions may be set for each region. For example, when two or more regions for which reduction of artifacts is desired locate at remote positions, these regions may be set at each region. With such a configuration, the $B_1$ value can be more locally suppressed to effectively reduce artifacts.

Further, for example, when a constraint condition that the $B_1$ average of the suppression region is suppressed is set as in the fourth optimization conditions, different values may be set as the predetermined value $B_U$ used in the constraint condition for two or more of the suppression regions. That is, the constraint condition may be weighted according to the position of the suppression region.

Further, although a two-dimensional imaging region is mainly shown in the drawings for explaining the aforementioned embodiment, the optimal radio frequency magnetic field conditions can be obtained also for a three-dimensional region in the same manner.

Further, the aforementioned embodiment is explained for a 3 T MRI apparatus and a transmission coil having four channels as examples, the configuration of the MRI apparatus is not limited to such a configuration. A magnetic field intensity higher than 3 T and a transmission coil having more than four of channels may also be used.

Furthermore, although the aforementioned embodiment is configured so that the computer 109 of the MRI apparatus 100 is provided with the RF shimming means 313, and calculates at least one of optimal amplitude and phase of RF, the present invention is not limited to such a configuration. For example, the RF shimming means 313 may be constructed on a computer independent from the MRI apparatus 100, which computer can transmit and receive data to and from the computer 109. Similarly, the condition storing means 304 may also be constructed on an independent storage device accessible by the computer 109, not the storage device 111 of the MRI apparatus 100.

Further, the method of this embodiment can be applied to various kinds of imaging regions including those for medical purposes.

DENOTATION OF REFERENCE NUMERALS

100: MRI Apparatus, 101: magnet, 102: gradient coil, 103: subject, 104: sequencer, 105: gradient magnetic field power supply, 106: radio frequency magnetic field generator, 107: table, 108: receiver, 109: computer, 110: display, 111: storage device, 112: shim coil, 113: shim power supply, 114: transmission coil, 114*a*: channel, 114*b*: channel, 114*c*: channel, 114*d*: channel, 115: reception coil, 117*a*: feeding point, 117*b*: feeding point, 117*c*: feeding point, 117*d*: feeding point, 200: phantom, 201: imaging region, 202: $B_1$ distribution, 301: region setting means, 302: condition setting means, 303: optimization means, 304: condition storing means, 310: imaging condition setting means, 311: imaging position setting means, 312: static magnetic field shimming means, 313: RF shimming means, 320: main scan means, 401: $B_1$ distribution, 402: $B_1$ distribution, 403: $B_1$ distribution, 404: $B_1$ distribution, 500: table, ROI1: first region, ROI2: second region

The invention claimed is:

1. A magnetic resonance imaging apparatus, comprising:
a transmission coil having multiple channels each for transmitting a radio frequency wave to a subject;
a region setter configured to set:
  a predetermined region in an imaging region as a first region, and
  a region in the imaging region and different from the first region as a second region, which is a region including a region that generates artifacts or a region that shows high specific absorption ratio; and
an optimization module configured to determine at least one of amplitude or phase of a radio frequency wave transmitted to each of the multiple channels as a radio frequency magnetic field condition,
  wherein the optimization module determines the radio frequency magnetic field condition by optimizing a uniformity of radio frequency magnetic field distribution in the first region at a same time as optimizing at least one of specific absorption ratio or signal value of a region that generates artifacts,
  wherein the optimized uniformity of radio frequency magnetic field distribution in the first region is not lower than a predetermined value,
  wherein the optimized at least one of specific absorption ratio or signal value of a region that generates artifacts is not higher than a predetermined value defined for each,
  wherein the optimization module uses at least one of the uniformity, specific absorption ratio, or signal value of a region that generates artifacts for the constraint condition, and at least one of the remainder for the objective function, calculates and determines the radio frequency magnetic field condition as a solution that optimizes the objective function,
  wherein the constraint condition is that the uniformity is not lower than a predetermined value, and
  wherein the objective function is such a function that, by minimizing a ratio of average of the radio frequency magnetic field in the first region and average of the radio frequency magnetic field in the second region, the signal value of the second region is made to be not higher than a predetermined value.

2. A magnetic resonance imaging apparatus, comprising:
a transmission coil having multiple channels each for transmitting a radio frequency wave to a subject;
a region setter configured to set:
  a predetermined region in an imaging region as a first region, and
  a region in the imaging region and different from the first region as a second region, which is a region including a region that generates artifacts or a region that shows high specific absorption ratio; and
an optimization module configured to determine at least one of amplitude or phase of a radio frequency wave transmitted to each of the multiple channels as a radio frequency magnetic field condition, wherein the optimization module determines the radio frequency magnetic field condition by optimizing a uniformity of radio frequency magnetic field distribution in the first region at a same time as optimizing at least one of specific absorption ratio or signal value of a region that generates artifacts, wherein the optimized uniformity of radio frequency magnetic field distribution in the first region is not lower than a predetermined value, wherein the optimized at least one of specific absorption ratio or signal value of a region that generates artifacts is not higher than a predetermined value defined for each, wherein the optimization module uses at least one of the uniformity, specific absorption ratio, or signal value of a region that generates artifacts for the constraint condition, and at least one of the remainder for the objective function, calculates and determines the radio frequency magnetic field condition as a solution that optimizes the objective function, wherein the constraint condition is that the uniformity is not lower than a predetermined value, and wherein the objective function is such a function that, by maximizing average of the radio frequency magnetic field in the first region, the signal value of the second region is made to be not higher than a predetermined value.

3. A magnetic resonance imaging apparatus, comprising:
a transmission coil having multiple channels each for transmitting a radio frequency wave to a subject;
a region setter configured to set:
  a predetermined region in an imaging region as a first region, and
  a region in the imaging region and different from the first region as a second region, which is a region including a region that generates artifacts or a region that shows high specific absorption ratio; and
an optimization module configured to determine at least one of amplitude or phase of a radio frequency wave transmitted to each of the multiple channels as a radio frequency magnetic field condition,
  wherein the optimization module determines the radio frequency magnetic field condition by optimizing a uniformity of radio frequency magnetic field distribution in the first region at a same time as optimizing at least one of specific absorption ratio or signal value of a region that generates artifacts,
  wherein the optimized uniformity of radio frequency magnetic field distribution in the first region is not lower than a predetermined value,
  wherein the optimized at least one of specific absorption ratio or signal value of a region that generates artifacts is not higher than a predetermined value defined for each,
  wherein the optimization module uses at least one of the uniformity, specific absorption ratio, or signal value of a region that generates artifacts for the constraint condition, and at least one of the remainder for the objective function, calculates and determines the radio frequency magnetic field condition as a solution that optimizes the objective function, and
  wherein the constraint condition is that the uniformity is not lower than a predetermined value, and is such a condition that, by making average of the radio frequency magnetic field in the second region not higher than a predetermined value, the signal value of the second region is made to be not higher than a predetermined value.

4. A magnetic resonance imaging apparatus, comprising:
a transmission coil having multiple channels each for transmitting a radio frequency wave to a subject;
a region setter configured to set:
  a predetermined region in an imaging region as a first region, and
  a region in the imaging region and different from the first region as a second region, which is a region including a region that generates artifacts or a region that shows high specific absorption ratio; and
an optimization module configured to determine at least one of amplitude or phase of a radio frequency wave transmitted to each of the multiple channels as a radio frequency magnetic field condition,
  wherein the optimization module determines the radio frequency magnetic field condition by optimizing a uniformity of radio frequency magnetic field distribution in the first region at a same time as optimizing at least one of specific absorption ratio or signal value of a region that generates artifacts,
  wherein the optimized uniformity of radio frequency magnetic field distribution in the first region is not lower than a predetermined value,
  wherein the optimized at least one of specific absorption ratio or signal value of a region that generates artifacts is not higher than a predetermined value defined for each,
  wherein the optimization module uses at least one of the uniformity, specific absorption ratio, or signal value of a region that generates artifacts for the constraint condition, and at least one of the remainder for the objective function, calculates and determines the radio frequency magnetic field condition as a solution that optimizes the objective function,
  wherein the objective function is such a function that, by minimizing the sum of irradiation powers of the radio frequency magnetic fields transmitted from channels near the second region among the multiple channels, specific absorption ratio is made to be not higher than a predetermined value, and
  wherein the constraint condition is that the uniformity is not lower than a predetermined value, and the specific absorption ratio (SAR) of the second region is not higher than a predetermined value.

* * * * *